United States Patent
Tzou et al.

[11] Patent Number: 5,922,895
[45] Date of Patent: Jul. 13, 1999

[54] AMINE BORANE COMPLEXES AND PHOSPHINEBORANE COMPLEXES AS CATALYST FOR HYDROSILATION

[75] Inventors: Ming-Shin Tzou, Midland, Mich.; Yasushi Sugiura, Chiba Prefecture, Japan

[73] Assignee: Dow Corning Corporation, Midland, Mich.

[21] Appl. No.: 09/062,076

[22] Filed: Apr. 17, 1998

[51] Int. Cl.$^6$ ....................................................... C07F 7/08
[52] U.S. Cl. .................................................................. 556/479
[58] Field of Search ............................................. 556/679

[56] References Cited

U.S. PATENT DOCUMENTS

| | | | |
|---|---|---|---|
| 2,823,218 | 2/1958 | Speier et al. | 260/448.2 |
| 3,220,972 | 11/1965 | Lamoreaux | 260/46.5 |
| 3,658,866 | 4/1972 | Tsuji et al. | 556/479 |
| 5,191,103 | 3/1993 | Mehta et al. | 556/479 |
| 5,262,554 | 11/1993 | Bank | 556/479 X |
| 5,621,129 | 4/1997 | Hayashi et al. | 556/479 X |
| 5,654,455 | 8/1997 | Pastor et al. | 556/479 X |

*Primary Examiner*—Paul F. Shaver
*Attorney, Agent, or Firm*—Melvin D. Fletcher

[57] ABSTRACT

A hydrosilation method comprising contacting a silicon hydride with an unsaturated reactant in the presence of a catalysts selected from the group consisting of amine borane complexes and phoshineborane complexes. The catalysts are especially useful for selectively hydrosilating unsaturated organic compounds with an internal unsaturated bond to increase the desired hydrosilation product yield.

17 Claims, No Drawings

AMINE BORANE COMPLEXES AND PHOSPHINEBORANE COMPLEXES AS CATALYST FOR HYDROSILATION

BACKGROUND OF INVENTION

The present invention is a hydrosilation method comprising contacting a silicon hydride with an unsaturated reactant in the presence of a catalyst selected from a group consisting of amine borane complexes and phosphineborane complexes. The catalyst are especially useful for increasing selectivity for the hydrosilation of unsaturated reactants where the unsaturation is in the internal portion of the reactant's structure.

It is known in the art to produce organosilicon compounds by reacting a silicon hydride containing compound with an unsaturated organic compound in the presence of a catalyst. This reaction is typically referred to as hydrosilation or hydrosilylation. Typically the catalyst is platinum metal on a support, a platinum compound generally in a solvent, or a platinum complex.

In Speier et al., U.S. Pat. No. 2,823,218, a method for the production of organosilicon compounds by reacting an Si-H with a compound containing aliphatic carbon atoms linked by multiple bonds in the presence of chloroplatinic acid is taught. Lamoreaux, U.S. Pat. No. 3,220,972, teaches a similar process, however the catalyst is a eaction product of chloroplatinic acid.

One major limitation platinum has as a hydrosilation catalyst is that it is not particularly effective hydrosilating unsaturated organic compounds with an internal unsaturated bond and is known to produce multiple hydrosilation products that are difficult to separate. In addition to multiple hydrosilation products, when platinum catalyst is used to hydrosilate unsaturated organic compounds with an internal unsaturated bond, often the result is migration of the unsaturated bond such that silyl group bonds to the terminal carbon.

The present invention provides a method for hydrosilating unsaturated reactants for the preparation of organosilanes. The inventors have unexpectedly discovered that catalysts selected from the group consisting of amine borane complexes and phosphineborane complexes can be used in hydrosilation reactions. More particularly, these catalysts can selectively hydrosilate unsaturated organic compounds with internal unsaturated bond to increase the desired hydrosilation product yield.

SUMMARY OF INVENTION

The present invention is a hydrosilation method comprising contacting a silicon hydride with an unsaturated reactant in the presence of a catalyst selected from the group consisting of amine borane complexes and phoshineborane complexes. The catalysts are especially useful for selectively hydrosilating unsaturated organic compounds with an internal unsaturated bond to increase the desired hydrosilation product yield.

DESCRIPTION OF INVENTION

The present invention is a hydrosilation method comprising contacting a silicon hydride with an unsaturated reactant in the presence of a catalyst selected from the group consisting of amine borane complexes and phoshineborane complexes. The method comprises contacting (A) a silicon hydride described by formula $R^1_a H_b SiX_{4-a-b}$ (1) where each $R_1$ is independently selected from the group consisting of alkyls comprising one to about 20 carbon atoms, cycloalkyls comprising four to about 12 carbon atoms, and aryls; X is a halogen, a=0 to 3, and a+b=1 to 4; and (B) an unsaturated reactant selected from the group consisting of
  (i) substituted and unsubstituted unsaturated organic compounds,
  (ii) silicon compounds comprising substituted or unsubstituted unsaturated organic substituents, and
  (iii) mixtures of (i) and (ii);

in the presence of a catalyst selected from the group consisting of amine borane complexes described by formula $R^2_3 NBH_3$ and phoshineborane complexes described by formula $R^2_3 PBH_3$, where each $R^2$ is independently selected from the group consisting of alkyls comprising one to about 10 carbon atoms, arylalkyl, and aryls.

The contacting of the silicon hydride with the unsaturated reactant can be effected in standard type reactors for conducting hydrosilation processes. The contacting may be conducted as a continuous, semi-continuous, or batch process.

Silicon hydrides useful in the present method are described by formula (1), where each $R_1$ is independently selected from the group consisting of alkyls comprising one to about 20 carbon atoms, cycloalkyls comprising four to about 12 carbon atoms, arylalkyls, and aryls; a=0 to 3, b=1 to 3, and a+b=1 to 4. $R^1$ can be, for example, a substituted or unsubstituted alkyl such as methyl, ethyl, propyl, butyl, pentyl, hexyl, heptyl, octyl, nonyl, decyl, undecyl, and dodecyl; a cycloalkyl such as cyclopropy, cyclobutyl, cyclopentyl, cyclohexyl, cycloheptyl, and cyclooctyl; an aryl such as phenyl, tolyl, and naphthyl. Preferred is when $R^1$ is methyl.

In formula (1), it is preferred that each $R^1$ be independently selected from a group consisting of alkyls comprising about one to six carbon atoms. Even more preferred is when each $R^1$ is methyl. X is a halogen and most preferred is when X is a chlorine atom.

Examples of silicon hydrides described by formula (1) which may be useful in the present method include trimethylsilane, dimethylsilane, triethylsilane, dichlorosilane, trichlorosilane, methyidichlorosilane, dimethylchlorosilane, ethyldichlorosilane, cyclopentyldichlorosilane, methylphenylchlorosilane, (3,3,3-trifluoropropyl)dichlorosilane, and methylchlorosilane. Examples of preferred silicon hydrides described by formula (1) include methyldichlorosilane, trichlorosilane and dichlorosilane.

The silicon hydride is contacted with an unsaturated reactant selected from a group consisting of (i) substituted and unsubstituted unsaturated organic compounds, (ii) silicon compounds comprising substituted and unsubstituted unsaturated organic substituents, and (iii) mixture of (i) and (ii). For purpose of this invention, "unsaturated" means that the compound contains at least one unsaturated bond.

More specific examples of the unsaturated reactants useful in the present method include unsubstituted cycloalkene compounds comprising at least four carbon atoms, substituted cycloalkene compounds comprising at least four carbon atoms, linear alkene compounds comprising two to about 30 carbon atoms, branched alkene compounds comprising four to about 30 carbon atoms, alkyne compounds comprising about two to 30 carbon atoms, and mixtures of two or more of any of the above.

The substituted and unsubstitued cycloalkene compounds useful in the present method are those containing one or more unsaturated bond in the ring. The unsubstituted cycloalkene compounds may be, for example, cyclobutene, cyclopentene, cyclohexene, cycloheptene, cyclooctene, 1,3-cyclohexadiene, 1,3,5-cycloheptatriene, 1-methylcyclopentene, 4-phenylcyclohexene, and 3-methylcyclopentadiene. The preferred cycloalkene compounds are cyclohexene and cyclopentene, with cyclohexene being the most preferred.

Unsaturated reactants useful in the present method include substituted and unsubstituted organic compounds including alkenes, such as, 1-hexene, 1,5-hexadiene, trans-2-hexene, 1-methyl-cyclohexene, 2-methyl-2-butene, 2,3-dimethyl-2-butene, 1,3-butadiene, 4-methyl-1,3-pentadiene, 2-methyl-3-hexene, 3-methyl-3-hexene, 3-ethyl-2,2-dimethyl-3-heptene, 4-methyl-2-hexene, 4-butyl-7-methyl-2-octene, 2,2,5,5-tetramethyl3-hexene, 2-pentene, 3-hexene, 2-methyl-2-pentene, 2,4,4-trimethyl-2-pentene, 3-methyl2-pentene, 4-methyl-2-pentene; and aryls, such as, styrene and α-methylstyrene. The method is especially useful for unsaturated reactants where the unsaturation is in the unsaturated reactant's internal structure.

Alkynes useful in the method are compounds comprising two to about 30 carbon atoms including, for example, 6-methyl-3-octyne, 2-butyne, 2-hexyne, 3-hexyne, 2-methyl-4-octyne, 5-decyne, and 2-pentyne.

The mole ratio of the unsaturated reactant to silicon hydride can be varied within a range of about 0.4:1 to 1.6:1. Preferred is when the mole ratio of unsaturated reactant to silicon hydride is within a range of about 0.8:1 to 1.2:1.

The silicon hydride and unsaturated reactant are contacted in the presence of a borane catalyst selected from the group consisting of amine borane complexes and phosphine borane complexes. The amine borane complexes useful in the method are described by formula $R^2_3NBH_3$, where each $R^2$ is independently selected from the group consisting of alkyls comprising one to about 10 carbon atoms, arylalkyl, and aryls. Substituent $R^2$ can be, for example, an alkyl such as methyl, ethyl, propyl, isopropyl, butyl, tertiary butyl, pentyl and hexyl; an arylalkyl such as benzyl; and an aryl such as phenyl and diphenyl.

The amine borane complexes can be trialkylamine boranes, such as, to trimethylamine borane, tricyclopentylamine borane, triphenylamine borane, dimethylbenzylamine borane, α-methylbenzyldimethylamine borane and triethylamine borane. Preferred is trimethylamine borane.

The phosphine borane complexes useful in the method are described by formula $R^2_3PBH_3$, where $R^2$ is as previously defined. Examples of phosphine borane complexes are, trimethylphosphine borane, tributylphosphine borane, triphenylphosphine borane, tri-p-tolylphosphine borane, and tri-9-phenanthrylphosphine borane. Preferred is triphenylphosphine borane.

The mole ratio of the unsaturated reactant to borane catalyst can be varied within a range of about 25:1 to 1000:1. Preferred is when the mole ratio of unsaturated reactant to borane catalyst is within a range of about 50:1 to 100:1.

The temperature at which the present method may be conducted can generally be within a range of about –10° C. to 260° C. It is preferred to conduct the method at a temperature within a range of about 150° C. to 170° C. The most preferred temperature for conducting the method is within a range of about 30° C. to 150° C.

The following examples are provided to illustrate the present invention. These examples are not intended to limit the claims herein.

EXAMPLE 1.

Evaluation of the hydrosilation of 2-methyl-2-butene with trichlorosilane. A 1:1 molar ratio solution of 2-methyl-2-butene and trichlorosilane was prepared in a glass tube without catalyst. The tube was heat sealed under an argon purge and heated at 250° C. for one hour. At the end of one hour the tube was cooled and the contents analyzed by $C^{13}$ nuclear magnetic resonance spectroscopy (NMR) and gas chromatography using a thermal conductivity detector (GC-TC). The GC-TC analysis indicated the formation of 2.8 area percent 2-methyl-3-trichlorosilylbutane under the GC-TC trace.

EXAMPLE 2.

Evaluation of the hydrosilation of 2-methyl-2-butene with trichlorosilane catalyzed by trimethylamine borane. A 50:50:1 molar ratio solution of 2-methyl-2-butene, trichlorosilane and trimethylamine borane was prepared in a glass tube. The tube was heat sealed under an argon purge and heated at 250° C. for one hour. At the end of one hour the tube was cooled and the contents analyzed by NMR and GC-TC. The GC-TC analysis indicated the formation of 31 area percent 2-methyl-3-trichlorosilylbutane.

EXAMPLE 3.

Evaluation of the hydrosilation of 1-methylcyclohexene with trichlorosilane without catalyst. A 1:1.26 molar ratio solution of 1-methylcyclohexene and $HSiCl_3$ was prepared in a glass tube. The tube was heat sealed under an argon purge and heated at 250° C. for one hour. At the end of one hour the tube was cooled and the contents analyzed by GC-TC. The analysis indicated the formation of 5 area percent 1-methyl-2-trichlorosilylcyclohexane.

EXAMPLE 4.

Evaluation of the hydrosilation of 1-methylcyclohexene with trichlorosilane catalyzed by trimethylamine borane. To a glass tube containing 12 g of the solution prepared in example 3 was added 0.066 g of trimethylamine borane. The tube was heat sealed under an argon purge and heated at 250° C. for one hour. At the end of one hour the tube was cooled and the contents analyzed by GC-TC. The analysis indicated the formation of 70 area percent 1-methyl-2-trichlorosilylcyclohexane.

EXAMPLE 5.

Evaluation of the hydrosilation of 1-methylcyclohexene with trichlorosilane catalyzed by triphenylphosphine borane. A 150:210:150:1 molar ratio solution of 1-methylcyclohexene, trichlorosilane, benzene as a solvent, and triphenylphosphine borane was prepared in a glass tube. The tube was heat sealed under an argon purge and heated at 210° C. for four hours. At the end of four hours the tube was cooled and the contents analyzed by GC-TC and NMR. The analysis indicated the formation of 54 area percent 1-methyl-2-trichlorosilylcyclohexane without any remaining 1-methylcyclohexene.

EXAMPLE 6.

Evaluation of the hydrosilation 2,3-dimethyl-2-butene with trichlorosilane catalyzed by trimethylamine borane. A 100:100:1 molar ratio solution of 2,3-dimethyl-2-butene, trichlorosilane, and trimethylamine borane was prepared in a glass tube. The tube was heat sealed under an argon purge and heated at 190° C. for four hours. At the end of four hours the tube was cooled and analyzed by GC-TC. The analysis indicated the formation of 22 area percent trichlorosilane, 21 area percent 2,3-dimethyl-2-butene, and 47 area percent 2,3-dimethyl-2-trichlorosily-butane. After 18 hours at 190° C. there was 5 area percent trichlorosilane, 3 area percent 2,3-dimethyl-2-butene, and 76 area percent 2,3-dimethyl-2-trichlorosilybutane.

EXAMPLE 7.

Evaluation of the hydrosilation 2,3-dimethyl-2-butene with methyldichlorosilane catalyzed by trimethylamine borane. A 100:20:1 molar ratio solution of 2,3-dimethyl-2-butene, methyldichlorosilane, and trimethylamine borane was prepared in a glass tube. The tube was heat sealed under an argon purge and heated at 250° C. for 0.5 hours. At the end of 0.5 hours the tube was cooled and analyzed by GC-TC. The analysis indicated the formation of 10 area percent 2-methyl-3methyldichlorosilylbutane. After 2 hour at 250° C., the analysis indicated the formation of 16 area percent 2-methyl-3-methyldichlorosilylbutane. After 18 hours at 230° C. the analysis indicated the formation of 19 area percent 2-methyl-3-methyldichlorosilylbutane.

We claim:

1. A hydrosilation method comprising contacting
   (A) a silicon hydride described by formula $R^1_a H_b SiX_{4-a-b}$
      where each $R^1$ is independently selected from the group consisting of alkyls comprising one to about 20 carbon atoms, cycloalkyls comprising four to about 12 carbon atoms, and aryls; X is a halogen, a=0 to 3, and a+b=1 to 4; and
   (B) an unsaturated reactant selected from the group consisting of
      (i) substituted and unsubstituted unsaturated organic compounds,
      (ii) silicon compounds comprising substituted or unsubstituted unsaturated organic substituents, and
      (iii) mixtures of (i) and (ii);
   in the presence of a catalyst selected from the group consisting of amine borane complexes described by formula $R^2_3 NBH_3$ and phosphineborane complexes described by formula $R^2_3 PBH_3$, where each $R^2$ is independently selected from the group consisting of alkyls comprising one to about 10 carbon atoms, arylalkyls, and aryls.

2. A method according to claim 1, where the silicon hydride is trichlorosilane.

3. A method according to claim 1, where the silicon hydride is methyldichlorosilane.

4. A method according to claim 1, where the amine borane complex is trimethylamineborane.

5. A method according to claim 1, where the phosphineborane complex is tripheylphosphineborane.

6. A method according to claim 1, where the unsaturated reactant has an internal unsaturated bond.

7. A method according to claim 1, where the unsaturated reactant is an alkene.

8. A method according to claim 1, where the unsaturated reactant is an alkyne.

9. A method according to claim 1, where X is chlorine.

10. A method according to claim 1, where the mole ratio of the unsaturated reactant to the silicon hydride within a range of about 0.4:1 to 1.6:1.

11. A method according to claim 1, where the mole ratio of the unsaturated reactant to the silicon hydride is within a range of about 0.8:1 to 1.2:1.

12. A method according to claim 1, where the mole ratio of the unsaturated reactant to the catalyst is within a range of about 25:1 to 1000:1.

13. A method according to claim 1, where the mole ratio of the unsaturated reactant to the catalyst is within a range of about 50:1 to 100:1.

14. A method according to claim 1, where contact of the silicon hydride with the unsaturated reactant is effected at a temperature within a range of about −10° C. to 260° C.

15. A method according to claim 1, where contact of the silicon hydride with the unsaturated reactant is effected at a temperature within a range of about 15° C. to 200° C.

16. A method according to claim 1, where contact of the silicon hydride with the unsaturated reactant is effected at a temperature within a range of about 30° C. to 150° C.

17. A hydrosilation method comprising contacting
   (A) a silicon hydride described by formula $R^1_a H_b SiX_{4-a-b}$
      where each $R^1$ is independently selected from the group consisting of alkyls comprising one to about 20 carbon atoms, cycloalkyls comprising four to about 12 carbon atoms, and aryls; X is a halogen, a=0 to 3, and a+b=1 to 4; and
   (B) an unsaturated reactant selected from the group consisting of
      (i) substituted and unsubstituted unsaturated organic compounds,
      (ii) silicon compounds comprising substituted or unsubstituted unsaturated organic substituents, and
      (iii) mixtures of (i) and (ii); where the unsaturated reactant has an internal unsaturated bond,
   in the presence of a catalyst selected from the group consisting of amine borane complexes described by formula $R^2_3 NBH_3$ and phosphineborane complexes described by formula $R^2_3 PBH_3$, where each $R^2$ is independently selected from the group consisting of alkyls comprising one to about 10 carbon atoms, arylalkyks, and aryls.

* * * * *

UNITED STATES PATENT AND TRADEMARK OFFICE
CERTIFICATE OF CORRECTION

PATENT NO. : 5,922,895
DATED : July 13, 1999
INVENTOR(S) : Ming-Shin Tzou and Yasushi Sugiura It is certified that error appears in the above-identified patent and that said Letters Patent is hereby corrected as shown below:

On the title page: Item [73]
Assignee should read, "Dow Corning Corporation, Midland, Mich. and Dow Corning Toray Silicone Company, Ltd., Tokyo, Japan."

Signed and Sealed this

Twentieth Day of June, 2000

*Attest:*

Q. TODD DICKINSON

*Attesting Officer*   *Director of Patents and Trademarks*